US011311040B2

(12) United States Patent
Piskorz et al.

(10) Patent No.: US 11,311,040 B2
(45) Date of Patent: Apr. 26, 2022

(54) METHODS OF REDUCING A CONCENTRATION OF FORMALDEHYDE IN AQUEOUS SOLUTIONS OF SUGAR CARBONYLS

(71) Applicant: Kerry Luxembourg S.à.r.l., Luxembourg (LU)

(72) Inventors: Jan Piskorz, Waterloo (CA); Piotr Majerski, Waterloo (CA)

(73) Assignee: Kerry Group Services International Limited, Tralee (IE)

( * ) Notice: Subject to any disclaimer, the term of this patent is extended or adjusted under 35 U.S.C. 154(b) by 0 days.

(21) Appl. No.: 16/503,962

(22) Filed: Jul. 5, 2019

(65) Prior Publication Data
US 2019/0320695 A1 Oct. 24, 2019

Related U.S. Application Data

(62) Division of application No. 15/491,339, filed on Apr. 19, 2017.

(51) Int. Cl.
*A23L 13/50* (2016.01)
*A23L 5/20* (2016.01)
*A23L 27/21* (2016.01)
*A23L 27/30* (2016.01)
*A23L 5/10* (2016.01)

(52) U.S. Cl.
CPC ............ *A23L 13/55* (2016.08); *A23L 5/13* (2016.08); *A23L 5/20* (2016.08); *A23L 27/215* (2016.08); *A23L 27/33* (2016.08); *A23V 2002/00* (2013.01)

(58) Field of Classification Search
CPC . A23L 13/55; A23L 5/20; A23L 27/33; A23L 27/215; A23L 5/13
USPC ...................................................... 426/534
See application file for complete search history.

(56) References Cited

U.S. PATENT DOCUMENTS

| 5,393,542 | A | 2/1995 | Stradal et al. |
| 5,756,140 | A | 5/1998 | Shoop et al. |
| 7,094,932 | B2 | 8/2006 | Majerski et al. |
| 8,436,120 | B2 | 5/2013 | Piskorz et al. |
| 2004/0022912 | A1* | 2/2004 | Majerski ............. C07C 45/00 426/534 |
| 2015/0250198 | A1 | 9/2015 | Piskorz et al. |
| 2016/0002137 | A1 | 1/2016 | Taarning et al. |

FOREIGN PATENT DOCUMENTS

| JP | 2011-110079 A | 6/2011 |
| JP | 2012-528711 A | 11/2012 |
| WO | 2005/044917 A1 | 5/2005 |

OTHER PUBLICATIONS

NPL Ratner et al. (in J Am. Chem. Soc. vol. 59 (1) , pp. 200-206, 1937). (Year: 1937).*
NPL Ruiter et al. (in Food Technol. pp. 54-63, 1979 ). (Year: 1979).*
NPL Hayashi et al. (in Agric. Biol. Chem. 50 (8): 1965-1970, 1986). (Year: 1986).*
NPL Kallen et al. (In J Am Chem Soc. 93, pp. 6236-6247, 1971) (Year: 1971).*
NPL 23 amino acids (Retrieved on Sep. 21, 2020) (Year: 2020).*
NPL Rhia et al. (J Food Sci. 58(3), pp. 671-674, 1993). (Year: 1993).*
NPL Yasuhiro et al. (JP 2011-110079 equivalent priority date JP 2009-266048 A , Abstract English translation was submitted by the applicant on Mar. 11, 2022). The detailed machine translation is also used for review and attached as NPL Yasuhiro et al.). (Year: 2011).*
C.G.A. Davies & T.P. Labuza, "The Maillard Reaction Application to Confectionery Products", Confectionery Science, 1 1997.
Hayahi & Namiki, "Role of Sugar Fragmentation in an Early Stage Browning of Amino-carbonyl Reaction of Sugar with Amino Acid", Agricultural, Biology, Chemistry, vol. 50 (8), pp. 1965-1970, 1986.
Abraham F. Jalbout & Md. Abul Haider Shipar, "Formation of pyrazines in hydroxyacetaldehyde and glycine nonezymatic browning Maillard reaction: A computational study", Food Chemistry, vol. 103, pp. 1208-1216, 2007.
International Searching Authority, "International Search Report and the written opinion for PCT/CA2018/050741", dated Aug. 31, 2018.
Hodge, "Dehydrated Foods, Chemistry of Browning Reactions in Model Systems", Journal of Agricultural and Food Chemistry, 1953, pp. 928-943,1 (15).
Ruiter, "Color of smoked foods", Food Technology, 1979, pp. 54-63.
Ratner, et al., "The Action of Formaldehyde upon Cysteine", Journal of the American Chemical Society, 1937, pp. 200-206, 59(1).
Gerrard, et al., "Maillard crosslinking of food proteins I: the reaction of glutaraldehyde, formaldehyde and glyceraldehyde with ribonuclease", Food Chemistry, 2002, pp. 343-349, vol. 79, Issue 3.
Zhang, et al., "A Perspective on the Maillard Reaction and the Analysis of Protein Glycation by Mass Spectrometry: Probing the Pathogenesis of Chronic Disease", Journal of Proteome Research, 2009, pp. 754-769, 8 (2).
Communication dated Jan. 4, 2022 from the Japanese Patent Office in Japanese Application No. 2019-556364.

* cited by examiner

Primary Examiner — Donald R Spamer
Assistant Examiner — Bhaskar Mukhopadhyay
(74) Attorney, Agent, or Firm — Sughrue Mion, PLLC

(57) ABSTRACT

A method of reducing a concentration of formaldehyde in an aqueous solution containing formaldehyde, hydroxyacetaldehyde and other sugar carbonyls is provided. The method includes adding an amino acid to the aqueous solution and maintaining the aqueous solution at a temperature for a duration sufficient for the formaldehyde and the amino acid to react according to a Maillard reaction to produce a final concentration of formaldehyde and a final concentration of hydroxyacetaldehyde in the aqueous solution. The final concentration of formaldehyde is substantially lower than an initial concentration of formaldehyde and the final concentration of hydroxyacetaldehyde is not substantially lower than an initial concentration of hydroxyacetaldehyde. An aqueous solution and a method of browning a foodstuff are also provided.

32 Claims, No Drawings

METHODS OF REDUCING A CONCENTRATION OF FORMALDEHYDE IN AQUEOUS SOLUTIONS OF SUGAR CARBONYLS

CROSS REFERENCE TO RELATED APPLICATIONS

This application is a divisional of U.S. patent application Ser. No. 15/491,339, filed on Apr. 19, 2017, the contents of which is incorporated herein by reference in its entirety.

TECHNICAL FIELD

The embodiments disclosed herein relate to methods of providing an aqueous solution with a reduced concentration of formaldehyde, and more specifically, to methods of providing an aqueous solution with a reduced concentration of formaldehyde, the solution including hydroxyacetaldehyde and other sugar carbonyl compounds.

BACKGROUND

Pyrolysis of sugars (such as glucose) is a known reaction that has been shown to be useful for producing solutions comprising hydroxyacetaldehyde (also called glycolaldehyde). For example, as shown in U.S. Pat. No. 7,094,932, the pyrolysis of glucose can provide commercially useful yields of aqueous solutions comprising hydroxyacetaldehyde. These aqueous solutions can be useful in the food industry as natural browners (e.g. for meats, fish, and bakery items), as flavor precursors, as proteinaceous crosslinkers and as antimicrobial solutions.

During the pyrolysis of glucose, formaldehyde is produced as an undesirable by-product. Formaldehyde is particularly undesirable in aqueous solutions comprising hydroxyacetaldehyde intended to be used in the food industry as gaseous formaldehyde is well known to be a hazardous substance to humans.

U.S. Patent App. No. 2016/0002137 teaches one method of removing formaldehyde from a solution comprising hydroxyacetaldehyde. The method uses reactive distillation in the presence of an alcohol and a catalyst to remove formaldehyde from the solution comprising hydroxyacetaldehyde, where the formaldehyde is selectively acetalized. Although the product of the reactive distillation is substantially free of formaldehyde, the formaldehyde acetals formed during the reactive distillation must be separately removed from the product solution prior to use of the product solution in the subsequent catalytic hydrogenation of hydroxyacetaldehyde to ethylene glycol.

Accordingly, there is a need for an improved method of reducing a concentration of formaldehyde in aqueous solutions comprising sugar carbonyls.

SUMMARY

In accordance with one aspect, a method of reducing a concentration of formaldehyde in an aqueous solution containing formaldehyde, hydroxyacetaldehyde and other sugar carbonyls is provided. The method includes adding an amino acid to the aqueous solution and maintaining the aqueous solution at a temperature for a duration sufficient for the formaldehyde and the amino acid to react according to a Maillard reaction to produce a final concentration of formaldehyde and a final concentration of hydroxyacetaldehyde in the aqueous solution. The final concentration of formaldehyde is substantially lower than an initial concentration of formaldehyde in the aqueous solution and the final concentration of hydroxyacetaldehyde is not substantially lower than an initial concentration of hydroxyacetaldehyde in the aqueous solution.

In another aspect of the method, the final concentration of formaldehyde is less than 50% of the initial concentration of formaldehyde.

In another aspect of the method, the final concentration of formaldehyde is less than 10% of the initial concentration of formaldehyde.

In another aspect of the method, the final concentration of hydroxyacetaldehyde is more than 50% of the initial concentration of hydroxyacetaldehyde.

In another aspect of the method, the final concentration of hydroxyacetaldehyde is more than 80% of the initial concentration of hydroxyacetaldehyde.

In another aspect of the method, the amino acid is one of glycine and cysteine.

In another aspect of the method, the amino acid is cysteine.

In another aspect of the method, the aqueous solution has an initial amount of formaldehyde and an amount of amino acid is added to the aqueous solution, wherein a molar ratio of the amount of amino acid added to the solution to the initial amount of formaldehyde is in a range of 1:2 to 1:10.

In another aspect of the method, the molar ratio is in a range of 1:3 to 1:5.

In another aspect of the method, the other sugar carbonyls further comprise one or more of glyoxal, pyruvaldehyde and acetol.

In another aspect of the method, the aqueous solution has an initial concentration of glyoxal, an initial concentration of pyruvaldehyde, an initial concentration of acetol, a final concentration of glyoxal, a final concentration pyruvaldehyde and a final concentration acetol; wherein the final concentration of glyoxal is not substantially lower than the initial concentration of glyoxal, the final concentration of pyruvaldehyde is not substantially lower than the initial concentration of pyruvaldehyde and the final concentration of acetol is not substantially lower than the initial concentration of acetol.

In another aspect, a method of browning a foodstuff is provided. The method includes preparing an aqueous solution of sugar carbonyls by pyrolysis of sugars, the sugar carbonyls comprising formaldehyde and hydroxyacetaldehyde, the aqueous solution having an initial concentration of formaldehyde and an initial concentration of hydroxyacetaldehyde, adding an amino acid to the aqueous solution, maintaining the aqueous solution at a temperature for a duration sufficient for the formaldehyde and the amino acid to react according to a Maillard reaction to produce a final concentration of formaldehyde and a final concentration of hydroxyacetaldehyde in the aqueous solution, wherein the final concentration of formaldehyde is substantially lower than the initial concentration of formaldehyde and the final concentration of hydroxyacetaldehyde is not substantially lower than the initial concentration of hydroxyacetaldehyde, and heating the aqueous solution with the final concentration of formaldehyde in the presence of the foodstuff to brown the foodstuff.

In another aspect of the method, the final concentration of formaldehyde is less than 10% of the initial concentration of formaldehyde.

In another aspect of the method, the final concentration of hydroxyacetaldehyde is more than 80% of the initial concentration of hydroxyacetaldehyde.

In another aspect of the method, the amino acid is one of glycine and cysteine.

In another aspect of the method, the amino acid is cysteine.

In another aspect, an aqueous solution of sugar carbonyls prepared by pyrolysis of sugars is provided. The sugar carbonyls include formaldehyde and hydroxyacetaldehyde. The aqueous solution has a final concentration of formaldehyde that is substantially lower than an initial concentration of formaldehyde and a final concentration of hydroxyacetaldehyde that is not substantially lower than an initial concentration of hydroxyacetaldehyde. The final concentration of formaldehyde and the final concentration of hydroxyacetaldehyde are produced by adding an amino acid to the aqueous solution and maintaining the aqueous solution at a temperature for a duration sufficient for the formaldehyde and the amino acid to react according to a Maillard reaction to produce the final concentration of formaldehyde and the final concentration of hydroxyacetaldehyde in the aqueous solution.

In another aspect of the solution, the final concentration of formaldehyde is less than 10% of the initial concentration of formaldehyde.

In another aspect of the solution, the final concentration of hydroxyacetaldehyde is more than 80% of the initial concentration of hydroxyacetaldehyde.

In another aspect of the solution, the amino acid is cysteine.

Additional aspects will be apparent in view of the description which follows. It should be understood however that the detailed description and the specific examples, while indicating preferred embodiments of the invention, are given by way of illustration only, since various changes and modifications will become apparent to those skilled in the art from this detailed description.

DETAILED DESCRIPTION

Various methods will be described below to provide an example of one or more embodiments. No embodiment described below limits any claimed embodiment and any claimed embodiment may cover methods that differ from those described below. The claimed embodiments are not limited to methods having all of the features of any one method described below or to features common to multiple or all of the methods described below. Any embodiment disclosed below that is not claimed in this document may be the subject matter of another protective instrument, for example, a continuing patent application, and the applicants, inventors or owners do not intend to abandon, disclaim or dedicate to the public any such embodiment by its disclosure in this document.

Herein, the term "Maillard reaction" refers to a chemical reaction between amino acids and reducing sugars. In the food industry, Maillard reactions are used as a form of non-enzymatic browning, where carbonyl groups of sugar-carbonyl compounds react with nucleophilic amino groups of amino acids in proteins to form a complex mixture of poorly characterized molecules. In food processing applications, the complex mixture of poorly characterized molecules can be responsible for a range of aromas, colors and flavors. Maillard reactions can include a series of consecutive reactions affecting food and biopharmaceutical products involving dozens of compounds. In the process, hundreds of different flavor compounds can be created. These compounds, in turn, break down to form yet more new flavor compounds, and so on. Each type of food has a very distinctive set of flavor compounds that are formed during the Maillard reaction. It is these same compounds that flavor scientists have used over the years to make a variety of flavors.

In one example, a Maillard reaction begins with a carbonyl group of a sugar reacting with an amino group of an amino acid, producing N-substituted glycosylamine and water. The unstable glycosylamine can then undergo Amadori rearrangement, forming an Amadori compound (e.g. ketosamines). Amadori rearrangement is an organic reaction describing the acid or base catalyzed isomerization or rearrangement reaction of the N-glycoside of an aldose or the glycosylamine to the corresponding 1-amino-1-deoxy-ketose. Returning to the Mallard reaction mechanism, there are several ways for the ketosamines to react further once undergoing Amadori rearrangement. For example, the ketosamines can produce two water molecules and reductones. Alternatively, diacetyl, aspirin, pyruvaldehyde and other short-chain sugar carbonyl hydrolytic fission products can be formed. Alternatively stiff, brown nitrogenous polymers and melanoidins can be produced. Melanoidins are complex, not well-characterized, nitrogeneous, water-soluble co-polymers which are responsible for brown coloration of foods. Specifically, melanoidin pigments are responsible for different shades of browning of smoked, baked, roasted and/or grilled foods, for example. Each type of food has a very distinctive set of flavor compounds and a different set of melanoidins are formed during the Maillard reaction based on the type of food.

Herein, the term "sugar carbonyl compounds" or "sugar carbonyls" refers to low molecular weight carbonyl compounds such as but not limited to formaldehyde, hydroxyacetaldehyde, glyoxal, pyruvaldehyde (also referred to as methylglyoxal) and acetol.

This application describes methods that use a Maillard reaction to reduce a concentration of formaldehyde in aqueous solutions with sugar carbonyls.

In one embodiment, the aqueous solution has an initial concentration of formaldehyde. For reference, formaldehyde is represented by the following formula I:

(I)

The initial concentration of formaldehyde in the aqueous solution can be in a range of 1 to 6 wt %. In an embodiment, the formaldehyde has an initial concentration in a range of 2 to 6 wt % and more specifically in a range of 3 to 6 wt % of the total weight of the aqueous solution.

The initial concentration of formaldehyde is reduced by adding an amino acid to the solution and maintaining the solution at a temperature for a duration for a Maillard reaction to occur and produce a final concentration of formaldehyde in the aqueous solution.

The final concentration of formaldehyde in the aqueous solution is substantially lower than the initial concentration of formaldehyde in the aqueous solution. Herein, a final concentration of a solute being "substantially lower" than an initial concentration of a solute refers to the final concentration of the solute being 50% or less of the initial concentration of the solute.

In an embodiment, the final concentration of formaldehyde in the aqueous solution may be less than 50% of the initial concentration of formaldehyde in the aqueous solution. In another embodiment, the final concentration of formaldehyde in the aqueous solution may be less than 40% of the initial concentration of formaldehyde in the aqueous solution. In another embodiment, the final concentration of formaldehyde in the aqueous solution may be less than 30% of the initial concentration of formaldehyde in the aqueous solution. In another embodiment, the final concentration of formaldehyde in the aqueous solution may be less than 20% of the initial concentration of formaldehyde in the aqueous solution. In another embodiment, the final concentration of formaldehyde in the aqueous solution may be less than 10% of the initial concentration of formaldehyde in the aqueous solution. In another embodiment, the final concentration of formaldehyde in the aqueous solution may be less than 5% of the initial concentration of formaldehyde in the aqueous solution.

In an embodiment, the final concentration of formaldehyde in the aqueous solution may be in a range of 0 to 2 wt % and more specifically in a range of 0 to 1 wt % of the total weight of the aqueous solution. In another embodiment, the final concentration of formaldehyde in the aqueous solution may be less than 0.5 wt % of the total weight of the aqueous solution. In another embodiment, the final concentration of formaldehyde in the aqueous solution may be less than 0.2 wt % of the total weight of the aqueous solution.

The aqueous solution also includes sugar carbonyls such as hydroxyacetaldehyde. For reference, hydroxyacetaldehyde is represented by the following formula II:

An initial concentration of hydroxyacetaldehyde in the aqueous solution can be in a range of 4 to 50 wt %. In an embodiment, the initial concentration of hydroxyacetaldehyde in the aqueous solution may be in a range of 20 to 30 wt % and more specifically in a range of 24 to 26 wt % of the total weight of the aqueous solution.

The initial concentration of hydroxyacetaldehyde in the aqueous solution is not substantially reduced by adding the amino acid to the aqueous solution and maintaining the aqueous solution at a temperature for a duration for the Maillard reaction to occur and produce a final concentration of hydroxyacetaldehyde in the aqueous solution.

The final concentration of hydroxyacetaldehyde in the aqueous solution is not substantially lower than the initial concentration of hydroxyacetaldehyde in the aqueous solution. Herein, a final concentration of a solute being "not substantially lower" than an initial concentration of a solute means that the final concentration of the solute is 50% or more of the initial concentration of the solute.

In an embodiment, the final concentration of hydroxyacetaldehyde in the aqueous solution may be more than 50% of the initial concentration of hydroxyacetaldehyde in the aqueous solution. In another embodiment, the final concentration of hydroxyacetaldehyde in the aqueous solution may be more than 60% of the initial concentration of hydroxyacetaldehyde in the aqueous solution. In another embodiment, the final concentration of hydroxyacetaldehyde in the aqueous solution may be more than 70% of the initial concentration of hydroxyacetaldehyde in the aqueous solution. In another embodiment, the final concentration of hydroxyacetaldehyde in the aqueous solution may be more than 80% of the initial concentration of formaldehyde in the aqueous solution.

In an embodiment, the final concentration of hydroxyacetaldehyde in the aqueous solution may be in a range of 4 to 50 wt %, more specifically in a range of 18 to 30 wt % and more specifically in a range of 20 to 25 wt % of the total weight of the aqueous solution.

In an embodiment, a molar ratio of an initial amount of hydroxyacetaldehyde in the aqueous solution to an initial amount of formaldehyde in the aqueous solution may be in a range of 10:1 to 2:1 and more specifically in a range of 5:1 to 3:1. In another embodiment, a molar ratio of a final amount of hydroxyacetaldehyde in the aqueous solution to a final amount of formaldehyde in the aqueous solution may be at least 50:1.

In an embodiment, the sugar carbonyls may include sugar carbonyls other than formaldehyde and hydroxyacetaldehyde. For example, the sugar carbonyls may further comprise one or more of glyoxal, pyruvaldehyde and acetol. The glyoxal may have an initial concentration in the aqueous solution in a range of 0.5 to 5 wt % and more specifically in a range of 1 to 5 wt % of the total weight of the aqueous solution. The pyruvaldehyde may have an initial concentration in the aqueous solution in a range of 0 to 5 wt % and more specifically in a range of 0 to 2 wt % of the total weight of the aqueous solution. The acetol may have an initial concentration in the aqueous solution in a range of 0 to 5 wt % and more specifically in a range of 0 to 3 wt % of the total weight of the aqueous solution. The glyoxal, pyruvaldehyde and acetol may combine to have a combined initial concentration in the aqueous solution in a range of 1 to 20 wt %, more specifically in a range of 1 to 15 wt % and more specifically in a range of 1 to 10 wt % of the total weight of the aqueous solution.

In an embodiment, each of the initial concentrations of glyoxal, pyruvaldehyde and acetol in the aqueous solution may not be substantially reduced by adding the amino acid to the solution and maintaining the solution at a temperature for a duration for the Maillard reaction to occur and produce final concentrations of each of the glyoxal, pyruvaldehyde and acetol in the aqueous solution.

In an embodiment, the final concentration of glyoxal in the aqueous solution may be in a range of 1 to 5 wt % and more specifically in a range of 2 to 5 wt % of the total weight of the aqueous solution. The final concentration of pyruvaldehyde in the aqueous solution may be in a range of 0 to 5 wt % and more specifically in a range of 0 to 2 wt % of the total weight of the aqueous solution. The final concentration of acetol in the aqueous solution may be in a range of 0 to 5 wt % and more specifically in a range of 0 to 3 wt % of the total weight of the aqueous solution. The glyoxal, pyruvaldehyde and acetol may combine to have a combined final concentration in the aqueous solution in a range of 1 to 10 wt % and more specifically in a range of 2 to 8 wt % of the total weight of the aqueous solution.

In an embodiment, the aqueous solution may further comprise water having an initial concentration in a range of 10 to 90 wt % and more specifically in a range of 50 to 70 wt % of the total weight of the aqueous solution and a final concentration in a range of 10 to 90 wt % and more specifically in a range of 50 to 70 wt % of the total weight of the aqueous solution.

As previously described, to reduce the initial concentration of formaldehyde in the aqueous solution, an amino acid is added to the aqueous solution.

The amino acid added to the aqueous solution may be selected from a group consisting of: alanine, arginine, asparagine, cysteine, glutamine, glycine, histidine, lysine, methionine, proline, serine, tryptophan, tyrosine, and valine. In one embodiment, the amino acid is selected from a group consisting of glycine and cysteine. In another embodiment, the amino acid can be one of glycine and cysteine. In another embodiment, the amino acid can be cysteine.

In an embodiment, the amino acid is added to the aqueous solution in an amount sufficient to produce a Maillard reaction between the amino acid and the formaldehyde. In one example, the amount of amino acid added to the aqueous solution is in a range of 1 to 5 wt % and more specifically in a range of 2 to 4 wt % of the total weight of the aqueous solution. In another example, the amount of amino acid added to the aqueous solution is such that a molar ratio of the amount of amino acid added to the aqueous solution to the amount of formaldehyde in the aqueous solution is in a range of 1:2 to 1:10. In another example, the amount of amino acid added to the aqueous solution is such that a molar ratio of the amino acid added to the aqueous solution to the formaldehyde in the aqueous solution is in a range of 1:3 to 1:5.

After adding the amino acid to the aqueous solution, the aqueous solution is maintained at a temperature for a duration sufficient to reduce the concentration of the formaldehyde in the aqueous solution resulting from the Maillard reaction between the amino acid and the formaldehyde. Upon mixing, the amino acid may dissolve in the aqueous solution.

In an embodiment the temperature of the aqueous solution may be maintained in a range of ~15° C. to 30° C. (e.g. room temperature) and more specifically in a range of ~18° C. to 22° C. to reduce the concentration of the formaldehyde in the aqueous solution as a result of the Maillard reaction between the amino acid and the formaldehyde.

In another embodiment, the temperature of the aqueous solution may be maintained for a duration in a range of 0 to 96 hours and more specifically from 48 to 96 hours to reduce the concentration of the formaldehyde in the aqueous solution as a result of the Maillard reaction between the amino acid and the formaldehyde.

In an embodiment, the amount of amino acid added to the aqueous solution is such that a molar ratio of the amount of amino acid added to the aqueous solution to the initial amount of formaldehyde in the aqueous solution is in a range of 1:2 to 1:10, and more specifically in a range of 1:3 to 1.5.

In an embodiment, after the Maillard reaction, the aqueous solution may further comprise melanoidins. Melanoidins are a product of the Maillard reaction. The structure of melanoidins is poorly defined as these heterogeneous macromolecular compounds cannot be individually characterized. Melanoidins include polymeric and colored final products of the Maillard reaction. Melanoidins can include furan ring- and nitrogen-containing co-polymers that vary in structure depending on the reactants and conditions of their preparation. Melanoidins can be responsible for a brown or red colour of roasted, baked, toasted, grilled, charred or browned foods, and are also common in many dietary liquids such as soy sauce, honey, wine, beer and coffee Melanoidins can be formed by cyclizations, dehydrations, retroaldolisations, rearrangements, isomerisations, and condensations that occur over the course of the Maillard reaction.

In one example, after the Maillard reaction, the aqueous solution may comprise melanoidins having a concentration in a range of 0-20 wt % and more specifically in a range of ~8-15 wt %. In another embodiment, after the Maillard reaction, the aqueous solution may comprise melanoidins having a concentration in a range of ~8-15 wt % when the initial concentration of formaldehyde in the aqueous solution was ~4 wt % and the initial concentration of hydroxyacetaldehyde in the aqueous solution was ~25 wt %.

In another embodiment, after the Maillard reaction, the aqueous solution may have a red colour. Optionally, the red colour of the aqueous solution can be removed by any known techniques such as but not limited to activated carbon or ion exchange resins application, membrane separation, nano-filtration or reverse osmosis.

In another embodiment, after providing the aqueous solution with the reduced concentration of formaldehyde, the aqueous solution may be used for browning foodstuffs. Herein, the term foodstuff refers to a substance suitable for consumption as food.

In an embodiment, a foodstuff may be browned by heating the foodstuff in the presence of the aqueous solution at a temperature for a duration sufficient to brown the foodstuff.

In an embodiment, of the method of browning a foodstuff, an aqueous solution of sugar carbonyls can be prepared by pyrolysis of sugars. The sugar carbonyls include formaldehyde and hydroxyacetaldehyde and the aqueous solution has an initial concentration of formaldehyde and an initial concentration of hydroxyacetaldehyde as previously described. An amino acid is added to the aqueous solution and the aqueous solution is maintained at a temperature for a duration sufficient for the formaldehyde and the amino acid to react according to a Maillard reaction to produce a final concentration of formaldehyde and a final concentration of hydroxyacetaldehyde in the aqueous solution as previously described. The final concentration of formaldehyde is substantially lower than the initial concentration of formaldehyde and the final concentration of hydroxyacetaldehyde is not substantially lower than the initial concentration of hydroxyacetaldehyde.

In an embodiment, the aqueous solution with the final concentration of formaldehyde may be heated in the presence of the food stuff to a temperature in a range of 60-150° C. In another embodiment, the foodstuff may be added to a heated aqueous solution while the aqueous solution is maintained at a temperature for a duration sufficient to cook the foodstuff. In an embodiment, the duration can be in a range of 2-5 minutes.

In an embodiment, heating the foodstuff in the aqueous solution with the final concentration of formaldehyde can produce a brownish colour on an exterior surface of the foodstuff, or applying the browning solution an exterior by other means.

In an embodiment, the foodstuff can be selected from: meat (e.g. sausage, bacon, etc.) fish, or baked items (e.g. a bakery or a pastry item).

EXAMPLES

In the following Examples, liquid products were quantified by HPLC analysis (Agilent, 1200 Series). The analytes were separated on a BioRad Aminex HPX-87H column operating at 30° C. The eluent was a 0.005 M aqueous $H_2SO_4$, at a flow rate of 0.6 mL/min. The analytes were quantified using Waters 410 RI detector against standard samples.

Example 1

To demonstrate reactivity between an amino acid and formaldehyde when the formaldehyde is in solution with hydroxyacetaldehyde, 1.5 moles of cysteine (product from Aldrich-Sigma) were added to a commercially available browning solution (ScanGold® distributed by Azelis) comprising 3.5 moles of hydroxyacetaldehyde and 1 mole of formaldehyde having a pH of ~2.5.

After 3 days at room temperature (e.g. between ~15-30° C.), a sample of the resulting aqueous solution was analyzed to determine its composition.

Formaldehyde was not present in the resulting aqueous solution and less than 0.5 moles of hydroxyacetaldehyde was present. Melanoidin formation was also demonstrated.

The resulting aqueous solution had a dark red appearance as expected for browning reaction and was not pungent.

Example 2

To demonstrate reactivity between an amino acid and formaldehyde when the formaldehyde is in solution with hydroxyacetaldehyde and other sugar carbonyl compounds, cysteine was added to a commercially available solution comprising ~4.5 wt % formaldehyde and ~30% hydroxyacetaldehyde such that the cysteine had a concentration of 3.6 wt % in the resulting aqueous solution. The solution was mixed until fully solubilized.

After 24 hours at room temperature (e.g. between ~15-30° C.), the formaldehyde concentration of the resulting solution was 1.5 wt % and the hydroxyacetaldehyde concentration of the resulting solution was still above 20 wt %.

Recalculating above results, one can see that roughly one mole of cysteine (molecular weight of 121.16 g/mol) is needed to react with approximately four moles of formaldehyde (molecular weight of 30.031 g/mol) with some losses of other carbonyls.

Example 3

In another example, 4.14 wt % of cysteine was added to a solution having 3.18 wt % of formaldehyde. No other carbonyls were present. After 4 days, white crystals appeared but the solution remained transparent and colourless. The formaldehyde concentration of the solution was reduced to 2.12 wt %. No browning reaction occurred. Based on the weight percentages of cysteine and formaldehyde and the molecular weights of cysteine and formaldehyde (provided above), it was determined that 0.034 moles of cysteine had reacted with 0.033 moles of formaldehyde (e.g. a molar ratio of ~1:1).

Example 4

In another example, cysteine was added at 4.0 wt % to a commercially available water-based solution containing sugar-carbonyls (ScanGold® distributed by Azelis). The initial water concentration of the solution was 65 wt %.

The product produced by the reaction between the cysteine and the commercially-available solution was stored at room temperature and re-analyzed over various time intervals. The results are provided in Table 1.

TABLE 1

| Carbonyl concentrations over time. | | | | |
|---|---|---|---|---|
| | Initial concentration (wt %) | Concentration after 2 hrs (wt %) | Concentration after 24 hrs (wt %) | Concentration after 4 days (wt %) |
| Hydroxyacetaldehyde | 25.5 | 22.2 | 20.1 | 20.0 |
| Formaldehyde | 3.4 | 1.6 | <0.6 | <0.5 |
| Glyoxal | 1.8 | 1.5 | 1.6 | 1.6 |
| Acetol | 1.3 | 1.1 | 1.1 | 1.1 |

The colour of the sample darkened over time to a dark, red color. After 4 days, the concentration of hydroxyacetaldehyde in the product stabilized and the pungent odour of formaldehyde was diminished.

Example 5

A variety of amino-acids were added in amounts of ~4.0 wt % to a commercially available water solution having the composition provided in Table 2:

TABLE 2

| Composition of a commercially-available aqueous solution. | |
|---|---|
| | Concentration (wt %) |
| Hydroxyacetaldehyde | 25.3 |
| Formaldehyde | ~3.3 |
| Glyoxal | ~2.0 |
| Methylglyoxal (pyruvaldehyde) | <1.0 |
| Acetol | ~1.4 |
| Water | ~65.0 |

All of the amino-acids used in the Examples described herein were obtained from Sigma-Aldrich.

Products of the commercially available solution after the addition of each of the amino acids listed in Table 3 (below) were kept for 4 days at room temperature and analyzed to determine the concentrations to hydroxyacetaldehyde and formaldehyde therein. The results are provided in Table 3:

TABLE 3

Results of hydroxyacetaldehyde and formaldehyde in the presence of various amino acids after 4 days.

| Amino acid | Hydroxyacetaldehyde concentration after 4 days (wt %) | Formaldehyde concentration after 4 days (wt %) | Colour of product solution |
|---|---|---|---|
| Glutamine | 23.2 | 1.4 | red |
| Asparagine | 22.5 | 1.0 | red |
| Arginine | 20.5 | 1.2 | red |
| Histidine | 20.5 | 1.7 | red |
| Tryptophan | 20.5 | 1.1 | solubility issue, orange |
| Glycine | 20.5 | 1.2 | red-dark |
| Serine | 20.5 | 1.5 | red |
| Lysine | 20.2 | 0.8 | red, deposit formed |
| Alanine | 19.7 | 1.0 | red-dark |
| Proline | 23 | 2.5 | yellow |
| Methionine | 22.5 | 1.5 | red |
| Valine | 23.5 | 1.2 | red |
| Tyrosine | 23.5 | 3.3 | yellow, not well soluble |
| Cysteine | 20 | <0.2 | red-dark |

It should be noted that the glyoxal, methylglyoxal and acetol concentrations in the product solutions did not change significantly from the original commercially available solution over the 4 day period. In the presence of hydroxyacetaldehyde, glyoxal, methylglyoxal and acetol, apart from tyrosine, all of the amino-acids tested affected the formaldehyde concentration of the product solution and contributed to the formation of brown/red co-polymers. Cysteine appeared to be the most efficient reducer of formaldehyde concentration.

Example 6

In another example, various amounts of cysteine (shown in Table 4 as weight percentages of the aqueous solution) were added to a solution comprising 24.9 wt % hydroxyacetaldehyde, 3.0 wt % formaldehyde, 22 wt % glyoxal, 1.5 wt % methylglyoxai and 1.4 wt % acetol. The samples reacted for ~3 days. The results are shown in Table 4.

TABLE 4

Hydroxyacetaldehyde and formaldehyde concentrations of product aqueous solutions after the addition of various amounts of cysteine.

| Cysteine (wt %) | Hydroxyacetaldehyde (wt %) | Formaldehyde (wt %) | Colour |
|---|---|---|---|
| 3.8 | 20 | <0.2 | red, very dark |
| 3.4 | 21 | <0.5 | red, very dark |
| 2.7 | 22 | <1.0 | red |
| 1.6 | 22.5 | 1.7 | orange/yellow |

The results appear to confirm the findings of previous Example 2 where a specific amount of cysteine to reduce the concentration of formaldehyde in the product aqueous solution and preserving (e.g. substantially preserving) the concentration of other sugar-carbonyls in the aqueous solution was 1 mole of cysteine for every 4 moles of formaldehyde in the original aqueous solution. It should further be noted that sample with 3.8 wt % of cysteine contained less than 0.04 wt % of formaldehyde.

As noted in Table 4, several of the sample solutions have a red colour after the Maillard reaction. The red colour can be removed by any appropriate, known technique such as but not limited to activated carbon or ion exchange resin applications, membrane separation, nano-filtration and/or reverse osmosis.

Example 7

In another example, testing similar to that described in Example 6 was conducted with another amino acid: glycine. The initial aqueous solution to which glycine was added had a composition of 25.5 wt % hydroxyacetaldehyde, 3.4 wt % formaldehyde, 2.0 wt % glyoxal and 1.4 wt % acetol. The samples reacted for ~3 days. The results are shown in Table 5.

TABLE 5

Hydroxyacetaldehyde and formaldehyde concentrations of aqueous solutions after the addition of various amounts of glycine.

| Glycine (wt %) | Hydroxyacetaldehyde (wt %) | Formaldehyde (wt %) | Colour |
|---|---|---|---|
| 7.0 | 14.0 | <0.2 | Dark, red |
| 4.8 | 20.0 | <0.8 | Dark, red |
| 3.5 | 22.0 | 1.4 | Dark, red |

Comparing the results shown in Tables 4 and 5, although glycine reacts with formaldehyde to reduce the concentration of formaldehyde in the product aqueous solution, the reaction between glycine and formaldehyde is not as efficient as the reaction between cysteine and formaldehyde. Roughly twice as much glycine than cysteine was used to achieve substantial removal of formaldehyde from the product aqueous solution (e.g. to reduce the concentration of formaldehyde in the aqueous solution to <0.2 wt %).

Table 6 shows four examples of samples with diluted solutions of hydroxyacetaldehyde. The water concentration in these samples is ~90 wt %. Various weight percentages of glycine were admixed/dissolved as indicated below.

TABLE 6

Hydroxyacetaldehyde and formaldehyde concentrations of sample aqueous solutions after the addition of various amounts of glycine.

| Sample | 1 | 2 | 3 | 4 |
|---|---|---|---|---|
| Glycine addition (wt %) | none | 0.33 | 0.88 | 1.8 |
| Hydroxyacetaldehyde (wt %) | 5.46 | 5.38 | 5.01 | 4.27 |
| Formaldehyde (wt %) | 0.73 | 0.49 | 0.27 | <0.2 |
| Glyoxal (wt %) | 0.42 | 0.35 | 0.24 | 0.18 |
| Acetol (wt %) | 0.35 | 0.30 | 0.30 | 0.31 |
| Colour | Light yellow | Yellow | Orange | red |

The solutions of Table 6 show that ~1 mole of glycine (mw ~75) reacts with ~1.3 moles of formaldehyde while sacrificing ~0.65 moles of hydroxyacetaldehyde. Accordingly, more hydroxyacetaldehyde is sacrificed than shown in Example 6 for cysteine.

Example 8

Raw pork sausages (product of Maple Leaf Co.) were inserted into the boiling hydroxyacetaldehyde/formaldehyde solution resulting from Example 1, containing 3.8 wt % cysteine, diluted 25 times. The solution was aged for approximately three days before being applied to pork sausages.

After approximately two minutes in the boiling solution, the sausages were removed and visually inspected. The sausages were a brown "roasted" colour and were ready to be consumed. The overall look and taste of the sausages were very positive (e.g. the sausages had a non-descriptive meaty flavor).

To compare the appearance of these sausages to traditional methods of boiling raw pork sausages, raw pork sausages of the same type (product of Maple Leaf Co.) were prepared in boiled water only, again for two minutes.

After removal from the boiling water, the appearance and taste of the sausages was inspected. The appearance and taste of the sausages from the boiled water were inferior when compared to the appearance and taste of the sausages boiled in the commercially-available solution mixed with cysteine. The sausages boiled in water only were described as tasting rather bland and they did not have the brown "roasted" colour of the sausages boiled in the solution resulting from Example 1.

While the above description provides examples of one or more methods or systems, it will be appreciated that other methods or systems may be within the scope of the claims as interpreted by one of skill in the art.

What is claimed is:

1. A method of browning a foodstuff comprising:
    a) preparing an aqueous solution of sugar carbonyls by pyrolysis of sugars, the sugar carbonyls comprising formaldehyde and hydroxyacetaldehyde, the aqueous solution having an initial concentration by weight of formaldehyde and an initial concentration by weight of hydroxyacetaldehyde;
    b) adding cysteine to the aqueous solution;
    c) maintaining the aqueous solution at a temperature for a duration sufficient for the formaldehyde and the cysteine to react according to a Maillard reaction to produce melanoidins, a final concentration by weight of formaldehyde, and a final concentration by weight of hydroxyacetaldehyde in the aqueous solution, wherein the final concentration by weight of formaldehyde is 50% or less than the initial concentration by weight of formaldehyde and the final concentration by weight of hydroxyacetaldehyde is 50% or more than the initial concentration by weight of hydroxyacetaldehyde; and
    d) heating the aqueous solution with the melanoidins, the final concentration of formaldehyde, and the final concentration of hydroxyacetaldehyde in the presence of the foodstuff to brown the foodstuff.

2. The method of claim 1, wherein the final concentration by weight of formaldehyde is less than 10% of the initial concentration by weight of formaldehyde.

3. The method of claim 1, wherein the final concentration by weight of hydroxyacetaldehyde is more than 80% of the initial concentration by weight of hydroxyacetaldehyde.

4. The method of claim 1, wherein a molar ratio of the amount of the cysteine added to the aqueous solution to the initial amount of formaldehyde is in a range of 1:2 to 1:10.

5. The method of claim 1, wherein a molar ratio of the amount of the added cysteine to the aqueous solution to the initial amount of formaldehyde is in a range of 1:3 to 1:5.

6. The method of claim 2, wherein the final concentration by weight of hydroxyacetaldehyde is more than 80% of the initial concentration by weight of hydroxyacetaldehyde.

7. The method of claim 1, wherein the aqueous solution of sugar carbonyls obtained by the pyrolysis of sugars further comprises one or more selected from the group consisting of glyoxal, pyruvaldehyde, and acetol.

8. The method of claim 7, wherein after the Maillard reaction, a combined total concentration of glyoxal, pyruvaldehyde, and acetol in the aqueous solution is 1 to 10% by weight.

9. The method of claim 1, wherein the aqueous solution of sugar carbonyls obtained by the pyrolysis of sugars further comprises a combined total concentration of 1 to 20% by weight of one or more selected from the group consisting of glyoxal, pyruvaldehyde, and acetol.

10. The method of claim 1, wherein the aqueous solution of sugar carbonyls obtained by the pyrolysis of sugars further comprises glyoxal, pyruvaldehyde, and acetol.

11. The method of claim 10, wherein after the Maillard reaction, a combined total concentration of glyoxal, pyruvaldehyde, and acetol in the aqueous solution is 1 to 10% by weight of the aqueous solution.

12. The method of claim 1, wherein the aqueous solution of sugar carbonyls obtained by the pyrolysis of sugars further comprises a combined total concentration of 1 to 20% by weight of glyoxal, pyruvaldehyde, and acetol.

13. The method of claim 1, wherein after the Maillard reaction, the aqueous solution comprises from greater than 0 to 20% by weight of the melanoidins.

14. The method of claim 1, wherein after the Maillard reaction, the aqueous solution comprises from 8 to 15% by weight of the melanoidins.

15. The method of claim 13, wherein after the Maillard reaction, the final concentration of the hydroxyacetaldehyde is 4 to 50% by weight.

16. The method of claim 14, wherein after the Maillard reaction, the final concentration of the hydroxyacetaldehyde is 4 to 50% by weight.

17. A method of browning a foodstuff comprising:
    a) preparing an aqueous solution of sugar carbonyls by pyrolysis of sugars, the sugar carbonyls comprising formaldehyde and hydroxyacetaldehyde, the aqueous solution having an initial concentration by weight of formaldehyde and an initial concentration by weight of hydroxyacetaldehyde;
    b) adding glycine to the aqueous solution;
    c) maintaining the aqueous solution at a temperature for a duration sufficient for the formaldehyde and the glycine to react according to a Maillard reaction to produce melanoidins, a final concentration by weight of formaldehyde, and a final concentration by weight of hydroxyacetaldehyde in the aqueous solution, wherein the final concentration by weight of formaldehyde is 50% or less than the initial concentration by weight of formaldehyde and the final concentration by weight of hydroxyacetaldehyde is 50% or more than the initial concentration by weight of hydroxyacetaldehyde; and
    d) heating the aqueous solution with the melanoidins, the final concentration of formaldehyde, and the final concentration of hydroxyacetaldehyde in the presence of the foodstuff to brown the foodstuff.

18. The method of claim 17, wherein the final concentration by weight of formaldehyde is less than 10% of the initial concentration by weight of formaldehyde.

19. The method of claim 17, wherein the final concentration by weight of hydroxyacetaldehyde is more than 80% of the initial concentration by weight of hydroxyacetaldehyde.

20. The method of claim 17, wherein a molar ratio of the amount of the glycine added to the aqueous solution to the initial amount of formaldehyde is in a range of 1:2 to 1:10.

21. The method of claim 17, wherein a molar ratio of the amount of the glycine added to the aqueous solution to the initial amount of formaldehyde is in a range of 1:3 to 1:5.

22. The method of claim 18, wherein the final concentration by weight of hydroxyacetaldehyde is more than 80% of the initial concentration by weight of hydroxyacetaldehyde.

23. The method of claim 17, wherein the aqueous solution of sugar carbonyls obtained by the pyrolysis of sugars further comprises one or more selected from the group consisting of glyoxal, pyruvaldehyde, and acetol.

24. The method of claim 23, wherein after the Maillard reaction, a combined total concentration of glyoxal, pyruvaldehyde, and acetol in the aqueous solution is 1 to 10% by weight.

25. The method of claim 17, wherein the aqueous solution of sugar carbonyls obtained by the pyrolysis of sugars further comprises a combined total concentration of 1 to 20% by weight of one or more selected from the group consisting of glyoxal, pyruvaldehyde, and acetol.

26. The method of claim 17, wherein the aqueous solution of sugar carbonyls obtained by the pyrolysis of sugars further comprises glyoxal, pyruvaldehyde, and acetol.

27. The method of claim 26, wherein after the Maillard reaction, a combined total concentration of glyoxal, pyruvaldehyde, and acetol in the aqueous solution is 1 to 10% by weight of the aqueous solution.

28. The method of claim 17, wherein the aqueous solution of sugar carbonyls obtained by the pyrolysis of sugars further comprises a combined total concentration of 1 to 20% by weight of glyoxal, pyruvaldehyde, and acetol.

29. The method of claim 17, wherein after the Maillard reaction, the aqueous solution comprises from greater than 0 to 20% by weight of the melanoidins.

30. The method of claim 17, wherein after the Maillard reaction, the aqueous solution comprises from 8 to 15% by weight of the melanoidins.

31. The method of claim 29, wherein after the Maillard reaction, the final concentration of the hydroxyacetaldehyde is 4 to 50% by weight.

32. The method of claim 30, wherein after the Maillard reaction, the final concentration of the hydroxyacetaldehyde is 4 to 50% by weight.

\* \* \* \* \*